US009596872B2

(12) United States Patent
Yamka et al.

(10) Patent No.: US 9,596,872 B2
(45) Date of Patent: Mar. 21, 2017

(54) COMPANION ANIMAL COMPOSITIONS INCLUDING PYRUVIC ACID AND SALTS THEREOF AND METHODS OF USE THEREOF

(75) Inventors: Ryan Michael Yamka, Topeka, KS (US); Nolan Zebulon Frantz, Meadville, PA (US); Steven C. Zicker, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 632 days.

(21) Appl. No.: 13/145,050

(22) PCT Filed: Jan. 15, 2010

(86) PCT No.: PCT/US2010/021189
§ 371 (c)(1),
(2), (4) Date: Sep. 23, 2011

(87) PCT Pub. No.: WO2010/083409
PCT Pub. Date: Jul. 22, 2010

(65) Prior Publication Data
US 2012/0004291 A1 Jan. 5, 2012

Related U.S. Application Data

(60) Provisional application No. 61/145,125, filed on Jan. 16, 2009, provisional application No. 61/224,249, filed on Jul. 9, 2009.

(51) Int. Cl.
| | | |
|---|---|---|
| *A61K 31/19* | (2006.01) | |
| *A61K 31/385* | (2006.01) | |
| *A61P 3/00* | (2006.01) | |
| *A61P 3/04* | (2006.01) | |

(52) U.S. Cl.
CPC ............. *A23K 50/48* (2016.05); *A23K 20/10* (2016.05); *A23K 20/121* (2016.05); *A23K 50/42* (2016.05); *A23V 2002/00* (2013.01)

(58) Field of Classification Search
CPC ............ A23V 2002/00; A23V 2200/30; A23V 2250/026; A23K 1/1618; A23K 1/1646; A23K 1/1853; A23K 1/1866; A23K 50/48; A23K 20/121; A23K 20/10; A23K 50/42
See application file for complete search history.

(56) References Cited

U.S. PATENT DOCUMENTS

| | | | |
|---|---|---|---|
| 4,351,835 A | 9/1982 | Stanko | |
| 5,339,771 A | 8/1994 | Axelrod | |
| 5,419,283 A | 5/1995 | Leo | |
| 5,621,117 A | 4/1997 | Bethge et al. | |
| 6,277,842 B1 | 8/2001 | Carthron | |
| 2003/0224061 A1 | 12/2003 | Pacioretty et al. | |
| 2004/0091572 A1* | 5/2004 | Bruce et al. | 426/2 |
| 2008/0214653 A1* | 9/2008 | Zicker et al. | 514/440 |
| 2009/0182032 A1* | 7/2009 | Zicker et al. | 514/440 |

FOREIGN PATENT DOCUMENTS

| | | |
|---|---|---|
| CN | 1404746 | 3/2003 |
| DE | 19836450 | 2/2000 |
| EP | 1875816 | 1/2008 |
| GB | 2344996 | 6/2000 |
| GB | 2344996 A * | 6/2000 |
| JP | 2007-153817 | 6/2007 |
| JP | 2007-308468 | 11/2007 |
| WO | WO 02/062329 | 8/2002 |
| WO | WO 2007/063095 | 6/2007 |
| WO | WO 2007/088046 | 8/2007 |

OTHER PUBLICATIONS

Machine Translation of DE 198 36 450 Al. Original Publication Date: Feb. 17, 2000. Translation Date: Feb. 20, 2014.*
AAFCO, 2004, American Association of Feed Control Officials, Official Publication pp. 129-137.
International Search Rpeort and Written Opinion in International Application No. PCT/US2010/021189, mailed May 27, 2010.

* cited by examiner

*Primary Examiner* — Sreeni Padmanabhan
*Assistant Examiner* — Jody Karol

(57) ABSTRACT

The invention encompasses pet food compositions and methods for the treatment and/or prevention of diseases or disorders in companion animals, for example, for the treatment or obesity, including administering a pet food composition including pyruvic acid or a salt thereof to a companion animal, or lipoic acid or salt thereof and pyruvic acid or a salt thereof to a companion animal. The invention encompasses pet food compositions and methods for managing weight including administering a pet food composition including pyruvic acid or a salt thereof, or lipoic acid or a salt thereof and pyruvic acid or a salt thereof to a companion animal to a companion animal.

13 Claims, No Drawings

COMPANION ANIMAL COMPOSITIONS INCLUDING PYRUVIC ACID AND SALTS THEREOF AND METHODS OF USE THEREOF

CROSS-REFERENCE TO RELATED APPLICATIONS

This application is a national stage entry under 35 U.S.C. §371 of International Patent Application No. PCT/US2010/021189, filed 15 Jan. 2010, which claims priority to U.S. Provisional Patent Application No. 61/145,125, which was filed 16 Jan. 2009 and U.S. Provisional Patent Application No. 61/224,249 which was filed 9 Jul. 2009, both of which are incorporated herein by reference in their entireties.

BACKGROUND OF THE INVENTION

An important indicator of animal health is the body composition of the animal. An unhealthy diet and/or an unhealthy lifestyle can result in the animal having an unhealthy proportion of body lap particularly in relation to lean muscle in she body, it is thought that, a body fat amount in excess of 30% by weight indicates that the animal is unhealthy, particularly if the amount of body fat is in excess of 35% by weight.

The invention encompasses pet food compositions for companion animals, which have increased therapeutic and prophylactic efficacy over currently marketed companion food products.

SUMMARY OF THE INVENTION

The inventors have developed food compositions and methods of using the compositions for treating or preventing disorders in animals.

Accordingly, the invention encompasses companion pet rood compositions meeting ordinary nutritional requirements of a net and including an effective amount of pyruvic acid or a salt thereof, or effective amounts of lipoic acid or a salt thereof and pyruvic acid or a salt thereof.

In all of these methods, it is desirable to administer the antioxidant or mixture thereof in the diet of the animal.

Another embodiment encompasses methods for maintaining or promoting a healthy body composition, for example, loss of weight or body fat, increased percentage of lean muscle mass in a companion animal, which includes feeding the animal a composition, including pyruvic acid or a salt thereof, or lipoic acid or a salt thereof and pyruvic acid or a salt thereof in an amount effective to promote or maintain the healthy body composition.

DETAILED DESCRIPTION OF THE INVENTION

General Description

The invention generally encompasses compositions comprising pyruvic acid or a salt thereof, or lipoic acid or a salt thereof and pyruvic acid or a salt thereof.

In certain embodiments, the pyruvic acid or a salt thereof is present in the composition, in an amount of 5 ppm to 20000 ppm.

In certain embodiments, the pyruvic acid or a salt thereof is present in the composition in an amount of 10 ppm to 10000 ppm.

In certain embodiments, the pyruvic acid or a salt thereof is present in the composition in an amount of 50 ppm to 5000 ppm.

In certain embodiments, the pyruvic acid or a salt thereof is present in the composition in an amount of 100 ppm to 2500 ppm.

In certain embodiments, the lipoic acid or a salt thereof is present in the composition in an amount of 5 ppm to 5000 ppm.

In certain embodiments, the lipoic acid or a salt thereof is present in the composition in an amount of 10 ppm to 4000 ppm.

In certain embodiments, the lipoic acid or a salt thereof is present in the composition in an amount of 50 ppm to 3000 ppm.

In certain embodiments, the book acid or a salt thereof is present in the composition in an amount of 100 ppm to 2000 ppm.

In certain embodiments, the lipoic acid or a salt thereof is present in the composition in an amount of 500 ppm to 1000 ppm.

In certain embodiments, the composition further comprises a protein, fat, carbohydrate, fiber, and combinations thereof.

In certain embodiments, the composition is a dog food.

In certain embodiments, the composition is a cat food.

In certain embodiments, the composition is a food, a nutritional diet, a supplement, an animal treat, or a toy.

In certain embodiments, the composition is in the firm of a moist food.

In certain embodiments, the composition is in the form of a dry food.

In another embodiment, the invention encompasses methods for managing weight in a companion animal, which comprises administering to the companion animal a composition comprising an effective amount of pyruvic acid or a salt thereof, or effective amounts of lipoic acid or a salt thereof and pyruvic acid or a salt thereof.

In certain embodiments, the administration is oral feeding.

Another embodiment of the invention encompasses methods for maintaining or promoting a healthy body composition in a companion animal, which includes feeding the animal a composition of the invention, which includes an effective amount of pyruvic acid or a salt thereof, or effective amounts of lipoic acid or a salt thereof and pyruvic acid or a salt thereof.

The term "companion animal" used in the present invention includes any non-human animal suitable for being kept as a pet by humans including a dog, a cat, and a rodent. All embodiments of the invention are preferably for the treatment of cats and/or dogs.

The term "dog" includes those dogs, which are companion annuals such as *Canis familiaris*, working dogs and the like. The term dog is synonymous with the term canine.

The term "cat" includes those cats, which are, companion auroras known as domestic cats or house cats.

The term "rodent" includes, but is not limited to, hamsters, mice, rats, guinea pigs, gerbils, rabbits, hedge bogs, ferrets, chinchillas etc.

All percentages expressed herein are by weight of the composition on dry matter basis unless specifically stated otherwise.

Compositions of the Invention

One embodiment of the invention encompasses compositions for companion annuals including pyruvic acid, or a salt thereof, or lipoic acid or a salt thereof and pyruvic acid or a salt thereof.

As used herein, the term "lipoic acid or a salt thereof" includes, but is not limited to, for example, alpha-lipoic acid, a racemic mixture of lipoic acids, a lipoate salt, ester, amide or derivative thereof for example as described in U.S. Pat. No. 5,621,117. In various embodiments, the lipoic acid can be administered in a composition comprising a wet or dry food composition, which may be in the form of a moist food, dry food, supplement or treat. The lipoic acid may be incorporated therein or on the surface of any food composition, such as, by spraying or precipitation thereon or may be added to the diet by way of snack, supplement, treat or in the liquid portion of the diet such as water or another fluid. The lipoic acid may be administered as a powder, solid or as a liquid including a gel. An important aspect is that the animal be provided an effective amount of the lipoic acid to provide a positive effect. Typically, the source of lipoic acid is present in the composition in an amount of up to an amount which remains non-toxic to the animal. Typical maximum quantities can vary from 10 to 5000 ppm. In certain embodiments, the range is from 100 ppm to 2500 ppm.

As used herein, the term "pyruvic acid or a salt thereof" includes, but is not limited to, for example, pyruvic acid or carboxylase anion of pyruvic acid known as pyruvate. In various embodiments, the pyruvic acid or a salt thereof can be administered in a composition comprising a wet or dry food composition, which may be in the form of a moist food, dry food, supplement or treat. The pyruvic acid or a salt thereof may be incorporated therein or on the surface of any food composition, such as, by spraying or precipitation thereon or may be added to the diet by way of snack, supplement, treat or in the liquid portion of the diet such as water or another fluid. The pyruvic acid or a salt thereof may be administered as a powder, solid or as a liquid including a gel. An important aspect is that the animal be provided an effective amount of the pyruvic acid or a salt thereof to provide a positive effect. Typically, the source of pyruvic acid or a salt thereof is present in the composition in an amount of up to an amount, which remains non-toxic to the animal. Typical maximum quantities can vary from 10 to 10000 ppm. In certain embodiments, the range is from 100 ppm to 5000 ppm.

As used herein, the term "salt" or "salt thereof" refers to acidic groups that may be present in compounds used in the present compositions. Lipoic acid and pyruvic acid are acidic in nature and are capable of forming base salts with various pharmacologically acceptable cations. Examples of such, salts include alkali metal or alkaline earth metal salts and, particularly, calcium, magnesium, sodium, lithium, zinc, potassium, and iron salts.

In various embodiments, a food composition comprising lipoic acid provides a substantially nutritionally complete diet for foe intended recipient animal. A "nutritionally complete diet" is a diet that includes sufficient nutrients for maintenance of normal health, of a healthy animal on the diet.

The quantity of lipoic acid can vary from 5 ppm to 5000 ppm, 10 ppm to 4000 ppm, 50 ppm to 3000 ppm, 100 ppm to 2000 ppm, 500 ppm to 1000 ppm. In various embodiments, the range of lipoic acid that can be administered dogs is 150 ppm to 4500 ppm. In various embodiments, the range of lipoic acid that can be administered cats is 65 ppm to 2600 ppm. In certain illustrative embodiments, quantities can vary from 5 ppm to an amount which remains non-toxic to the pet. In other embodiments, a range is from 100 ppm to 200 ppm.

The compositions of the invention include pyruvic acid or salt thereof in an amount effective to treat or prevent a disorder in a companion animal. Generally, the amount effective in the composition includes a source of pyruvic acid or salt thereof in an amount of from 5 ppm to 20000 ppm, 10 ppm to 10000 ppm, 50 ppm to 5000 ppm, 100 ppm to 3000 ppm. In certain embodiments, the pyruvic acid or salt thereof is in an amount of 100 to 3000 ppm, and in other embodiments, the pyruvic acid or salt thereof is in an amount of approximately 2000 ppm.

The combination of lipoic acid or salt thereof and pyruvic acid or salt thereof is present at a concentration that is not deleterious to the intended animal's health. Thus, for example, the lipoic acid or salt thereof is present at a concentration that does not cause undesirable or toxic effects.

The invention is based upon the discovery that adding a combination of lipoic acid or salt thereof and pyruvic acid or salt thereof to a composition for consumption by a companion animal provides treatment for obesity. Adding a combination of lipoic acid or salt thereof and pyruvic acid or salt thereof to a composition for consumption also decreases body fat and increases lean muscle mass.

The composition can be a liquid or a solid food. When the composition is a liquid, the lipoic acid or salt thereof and pyruvic acid or salt thereof can be admixed with other components. Where the composition is solid, the lipoic acid or salt thereof and pyruvic acid or salt thereof may be coated on the composition, incorporated into the composition, or both.

In various embodiments, the lipoic acid or salt thereof and pyruvic acid or salt thereof may be added to the animal's food. In various embodiments, the lipoic acid or salt thereof and pyruvic acid or salt thereof may be added to the animal's food by a compounder or manufacturer at a site or by an animal's caregiver prior to feeding the animal. In various embodiments, the lipoic acid or salt thereof and pyruvic acid or salt thereof may be added during the processing of an animal's food, such as during and/or after mixing of other components of the composition that is then packaged and made available to consumers. Such processing may include extrusion, canning, baking, and the like or any other method or process of producing pet foods that is known in the art. In various embodiments, the lipoic acid or salt thereof and pyruvic acid or salt thereof may be contributed by a natural source like an animal or plant component, or the lipoic acid or salt thereof and pyruvic acid or salt thereof may be contributed by a synthetically derived source, or the lipoic acid or salt thereof and pyruvic acid or salt thereof may be contributed by a mixture of natural and synthetic sources.

The compositions in addition to the lipoic seal or salt thereof and pyruvic acid or salt thereof include at least one component suitable for consumption by a companion animal including, but not limited to, fats, carbohydrates, proteins, fibers, nutritional balancing agents such as vitamins, minerals, and trace elements, and mixtures thereof. One of ordinary skill in the art can select the amount and type of food ingredients for a typical food based upon the dietary requirements of the animal, for example, the animal's species, age, size, weight, health, and function.

The food ingredient part of the food composition can include up to about 100% of any particular food ingredient or can include a mixture of food ingredients in various proportions. In certain embodiments, the food composition includes a combination of food ingredients in amounts of about 0 wt. % to 50 wt. % fat, 0 wt. % to 75 wt. % carbohydrate, 0 wt % to 95 wt. % protein, 0 wt. % to 40 wt. % dietary fiber, and 0 wt. % to 15 wt. % of one or more nutritional balancing agents.

In certain embodiments, the fat and carbohydrate food ingredient is obtained from a variety of sources such as animal fat, fish oil, vegetable oil, meat, meat by-products, grains, other animal or plant sources, and mixtures thereof. Grains include wheat, corn, barley, and rice.

In certain embodiments, the protein food ingredient is obtained horn a variety sources such as plants, animals, or both. Animal protein includes meat, meat by-products, dairy, and eggs. Meats include the flesh horn poultry, fish, and annuals such as cattle, swine, sheep, goats, and the like, meat by-products include lungs, kidneys, brain, livers, stomachs, and intestines. The protein, food ingredient may also be free amino acids and/or peptides. Preferably, the protein, food ingredient includes meat, a meat by-product, dairy products, or eggs.

In certain embodiments, the fiber food ingredient is obtained from a variety of sources such as vegetable fiber sources, for example, cellulose, beet pulp, peanut hulls, and soy fiber.

In certain embodiments, the nutritional balancing agents are obtained from a variety of sources known to skilled artisans, for example, vitamin and mineral supplements and food ingredients. Vitamins and minerals can be included in amounts required to avoid deficiency and maintain health. These amounts are readily available in the art. The National Research Council (NRC) provides recommended amounts of such nutrients for such animals. See, e.g., Nutrient Requirements of Swine (10th Rev. Ed., Nat'l Academy Press, Wash. D.C., 1998), Nutrient Requirements of Poultry (9th Rev. Ed., Nat'l Academy Press, Wash. D.C., 1994), Nutrient Requirements of Horses (5th Rev, Ed., Nat'l Academy Press, Wash. D.C., 1989). The American Feed Control Officials (AAFCO) provides recommended amounts of such nutrients for dogs and cats. See American Feed Control Officials, Inc., Official publication, pp. 129-137 (2004). Vitamins generally useful as food additives include vitamin A, vitamin B1, vitamin B2, vitamin B6, vitamin B12, vitamin D, biotin, vitamin R, folic acid, inositol, niacin, and pantothenic acid. Minerals and trace elements useful as food additives include calcium, phosphorus, sodium, potassium, magnesium, copper, zinc, chloride, iron, selenium, iodine, and iron.

In certain embodiments, the food compositions may contain additional ingredients such as vitamins, minerals, fibers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety effectors such as the particular components and ingredients included in the composition; the species of animal; the animal's age, body weight, general health, sex, and diet; the animal's consumption rate; the type of disease or condition being treated; and the like. Therefore, the component and ingredient amounts may vary widely and may deviate from the preferred proportions described herein.

In one illustrative embodiment, the composition may, for example, in addition to the lipoic acid or salt thereof and pyruvic acid or salt thereof also include at least one of the following:

(a) 0% to 75% carbohydrate,
(b) 2% to 50% fat,
(c) 0% to 40% dietary fiber, and
(d) 0% to 15% of one or more nutritional balancing agents.

The compositions can contain additional ingredients intended to maintain or improve the health of the animal, for example, supplements, medications, herbs, holistic drugs and compositions, and the like.

The composition of the invention may include one or more additional ingredients to prevent or treat one or more diseases or conditions. The component in the diet, which accomplishes this, is an antioxidant or mixture thereof. An antioxidant is a material that quenches a free radical. Examples of such materials include foods such as Ginkgo Biloba, citrus pulp, grape pomace, tomato pomace, carrot and spinach, all preferably dried as well as various other materials such as beta-carotene, selenium, coenzyme Q10 (ubiquinone), lutein, tocotrienols, soy isoflavones, S-adenosylmethionine, glutathione, taurine, N-acetylcysteine, Vitamin E, Vitamin C, alpha-lipoic acid, l-carnitine and the like. Vitamin E can be administered as a tocopherol or a mixture of tocopherols and various derivatives thereof such as esters like vitamin E acetate, succinate, palmitate, and the like. The alpha form is preferable but beta, gamma and delta forms can be included. The d form is preferable but racemic mixtures are acceptable. The firms and derivatives will function in a Vitamin E like activity after ingestion by the pet. Vitamin C can be administered in this diet as ascorbic acid and its various derivatives thereof such as calcium phosphate salts, cholesteryl salt, 2-monophosphate, and the like which will function in a vitamin C like activity after ingesting by the pet. They can be in any form such as liquid, semisolid, solid and boat stable form. L-carnitine can be administered in the diet and various derivatives of carnitine such as the salts such as the hydrochloride, fumarate and succinates, as well as acetylated carnitine, and the like can be used.

The quantities administered in the diet, all as wt % (dry matter basis) of the diet, are calculated as the active material, per se, that is measured as tree material. The maximum amounts employed should not bring about toxicity. At least about 100 ppm or at least about 150 ppm of Vitamin E can be used. A preferred range of 500 to 1,000 ppm can be employed. Although not necessary, a maximum of about 2000 ppm or about 1500 ppm is generally not exceeded. With respect to Vitamin C at least about 50 ppm is used, desirably at least about 75 ppm and mere desirably at least about 100 ppm. A non-toxic maximum can be employed. The quantity of lipoic acid can vary from at least about 25, desirably at least about 50 ppm, more desirably about 100 ppm. Maximum quantities can vary from 100 ppm to 600 ppm or to an amount which remains non-toxic to the pet. A preferred range is from 100 ppm to 200 ppm. For l-carnitine about 50 ppm, desirably about 200 ppm, more desirably about 300 ppm for canines are a useful minimum. For felines, slightly higher minimums of l-carnitine can be employed such as about 100 ppm, 200 ppm, and 500 ppm. A non-toxic maximum quantity can be employed, for example, less than about 5,000 ppm. For canines, lower quantities can be employed, for example, less than about 5,000 ppm. For canines, a preferred range is 200 ppm to 400 ppm. For felines, a preferred range is 400 ppm to 600 ppm. Beta-carotene at 1-15 ppm can be employed. Selenium at 0.1 up to 5 ppm can be employed. Lutein at least about 5 ppm can be employed. Tocotrienols at least about 25 ppm can be employed. Coenzyme Q10 at least about 25 ppm can be employed. S-adenosylmethionine at least about 50 ppm can be employed. Taurine at least about 1000 ppm can be employed. Soy isoflavones at least about 25 ppm can be used. N-acetylcysteine at least about 50 ppm can be used. Glutathione at least about 50 ppm can be used. Gingko Biloba at least 50 ppm of extract can be used.

In certain embodiments, the compositions further include an effective amount of at least one substance selected from the group consisting of glucosamine, chondroitin, chondroitin sulfate, methylsulfonylmethane ("MSM"), creatine, antioxidants, *Perna canaliculata*, omega-3 fatty acids, omega-6 fatty acids and mixtures thereof.

In certain embodiments, the composition can be a treat. Treats include compositions that are given to an animal to entice the animal to eat during a non-meal time, for example, dog bones for canines. Treats may be nutritional wherein the composition includes one or more nutrients or and may base a food-like composition. Non-nutritional treats encompass any other treats that are non-toxic. The composition or components are coated onto the treat, incorporated into the treat, or both. Treats of the invention can be prepared, by an extrusion or baking process similar to those used for dry food. Other processes also may be used to either coat the composition on the exterior of existing treat forms or inject the composition into an existing treat form.

In certain embodiments, the composition can be a toy. Toys include chewable toys such as artificial bones. The lipoic acid or a salt thereof can form a coating on the surface of the toy or on the surface of a component of the toy, be incorporated partially or fully throughout the toy, or both. In one embodiment, the lipoic acid or a salt thereof is orally accessible by the intended user. There are a wide range of suitable toys currently marketed, for example, U.S. Pat. No. 5,339,771, U.S. Pat. No. 5,419,283, and references disclosed therein. This invention provides both partially consumable toys, for example, toys including plastic components, and fully consumable toys, for example, rawhides and various artificial bones. The invention preferably provides toys for use by a dog or a eat.

Preparation of the Compositions of the Invention

The compositions of the invention may be prepared in a canned or wet form using conventional food preparation processes known to skilled artisans. Typically, ground animal proteinaceous tissues are mixed with the other Ingredients such as fish oils, cereal grams, balancing ingredients, special purpose additives (e.g. vitamin and mineral mixtures, inorganic salts, cellulose and beet pulp, bulking agents, and the like), the lipoic acid or salt thereof and pyruvic acid or salt thereof, and water in amounts sufficient for processing. These ingredients are mixed in a vessel suitable hit heating while blending the components. Heating of the mixture is effected using any suitable manner, for example, direct steam, injection or using a vessel fitted with a heat exchanger. Following the addition of the last ingredient, the mixture is heated to a temperature of about 50° F. to about 212° F. Temperatures outside this range are acceptable but may be commercially impractical without use of other processing aids. When heated to the appropriate temperature, the material will typically be in the form of a thick liquid. The thick liquid is filled into cans. A lid is applied, and the container is hermetically sealed. The sealed can is then placed info conventional equipment designed to sterilize the contents. Sterilization is usually accomplished by heating to temperatures of greater than about 230° F. for an appropriate time depending on the temperature used, the composition, and similar factors. The compositions of the present invention can be added to the food compositions before, during, or after preparation.

Food compositions may be prepared in a dry form using conventional processes known to skirled artisans. Typically, dry ingredients such as animal protein, plant protein, grains, and the lipoic acid or salt thereof and pyruvic acid or salt thereof are ground and mixed together. Moist or liquid ingredients, including fats, oils, animal protein, water, and the like are then added to and mixed with the dry mix. The mixture is then processed into kibbles or similar dry pieces. Kibble is often formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavours, fats, oils, powders, and the like. Kibble also can be made from the dough using a baking process, rather than extrusion, wherein the dough is placed into a mold before dry heat processing. The food compositions can be in the form of a treat using an extrusion or baking process similar to those described above for dry food or a toy such as those disclosed in U.S. Pat. Nos. 5,339,771 and 5,419,283.

In certain embodiments, the lipoic acid or salt thereof and pyruvic acid or salt thereof can be added to the food compositions before, during, or after preparation.

Methods of Treating or Preventing Disorders with Compositions of the Invention

The invention also encompasses methods of treating or preventing certain disorders by administering a therapeutically or prophylactically effective amount of a composition, including pyruvic acid or a salt thereof or lipoic acid or salt thereof and pyruvic acid or salt thereof to a companion animal in need thereof.

Another embodiment of the invention encompasses methods of treating or preventing an unhealthy body composition in a companion animal. In one embodiment, the method of treating or preventing an unhealthy body composition in a companion animal includes feeding the animal a composition including the pyruvic acid or salt thereof, or lipoic acid or salt thereof and pyruvic acid or salt thereof in an amount effective to treat or prevent the unhealthy body composition. The invention also encompasses the use of a composition including the pyruvic acid or salt thereof, or home acid or salt thereof and pyruvic acid or salt thereof for the manufacture of a medicament for the treatment or prevention of an unhealthy body composition in a companion animal.

In another embodiment an animal that is suffering from an unhealthy body composition is fed the composition of the Invention for a period until the animal reaches the desired body composition. The period is preferably at least 4 weeks, more preferably at least 6 weeks, and most preferably at least 8 weeks. This period depends on the animal's original body composition and the desired optimal body composition trying to be achieved. As used herein, an animal that is suffering from an unhealthy body composition has a body fat amount in excess of 30% by weight indicates that the animal generally is unhealthy, particularly if that amount of body fat is in excess of 35% by weight. A useful measure of healthy body composition is given by the body fat:lean muscle ratio. In certain embodiments, an unhealthy body composition includes a body fat:lean muscle weight ratio greater than 30:60. In other words, the body fat amount is 30% by weight, there is 68% by weight of muscle and the remaining 2% is bone. On the other hand, a good, healthy body composition includes a body fat:lean muscle weight ratio of around 20:78, indicating 20% fat and 78% lean muscle by weight. These values can be determined using DEXA (dual-energy x-ray absorptiometry). Cats fed a food containing the pyruvic acid or salt thereof, or lipoic acid or salt thereof and pyruvic acid or salt thereof lost significantly more weight, body fat, and increased percentage lean and percent bone mineral content compared to a similar control food. Dogs fed a food containing pyruvic acid or salt thereof, or lipoic acid or salt thereof and pyruvic acid or salt thereof alone had a higher percentage lean and less percent body fat. In addition, dogs fed the pyruvic acid or salt thereof, or lipoic acid or salt thereof and pyruvic acid or salt thereof alone had greater bone mineral density compared to the other foods, and less total fat than the control food and fish oil. This data suggests pyruvic acid or salt thereof, or lipoic acid or salt thereof and pyruvic acid or salt thereof has the unique ability to increase fat loss and improve body composition in ad libitum led dogs and cats.

In another aspect, the present invention provides a means for communicating information about or instructions for treating or preventing an unhealthy body composition in a companion annual. The communicating means includes a document, digital storage media, optical storage media, audio presentation, or visual display containing the information or instructions. Preferably, the communication is a displayed web site or a brochure, product label, package insert, advertisement, or visual display containing such information or instructions. Useful information includes one or more of (1) methods and techniques for administering the compositions and using the methods of the present invention, (2) details about the side effects, if any, caused by using the present invention, alone or in combination with other drugs, and (3) contact information for patients to use if they have a question, about the invention and its use. Useful instructions include dosages, administration amounts and frequency, and administration routes. The communication means is useful for instructing on the benefits of using the present invention and communicating the approved methods for using the invention.

The invention is not limited to the particular methodology, protocols, and reagents described herein because they may vary. Further, the terminology used herein is for the purpose of describing particular embodiments only and is not intended to limit the scone of the present invention. As used herein and in the appended claims, the singular forms "a," "an," and "the" include plural reference unless the content clearly dictates otherwise. Similarly, the words "Include", "includes", and "including" are to be interpreted inclusively rather than exclusively. Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof is relevant prior art for the present invention and the right to challenge the accuracy and pertinence of such patents, patent applications, publications, and other references is specifically reserved.

EXAMPLES

This invention, can be further illustrated by the following examples of preferred embodiments thereof, although it will be understood that these examples are included merely for purposes of illustration and are not intended to limit the scope of the invention unless otherwise specifically indicated.

Example 1

Thirty Two dogs were utilized in the weight loss study. All dogs began the study with % body fat (of total weight) greater than 34.8%. The dogs remained on the weight loss study for 4 months unless optimal body weight was achieved earlier (20% body fat). Dogs were allotted to one of four treatments (8 dogs per treatment; Tables 1, 2 and 3). Each food was kibbled and formulated in accordance with the Association of American Feed Control Officials (2005) nutrient guide for dogs and balanced to meet adult maintenance requirements. During the weight loss study all dogs underwent dual energy x-ray absorptiometry (DEXA) at mouths 0, 1, 2, 3, and 4. Following weight loss the dogs remained on the same roods for a period of 4 months to determine, if the food would prevent weight regain. During the maintenance portion of the study dogs underwent DEXA at months 0, 2 and 4. Blood chemistry screens were also analyzed at all DEXA timepoints.

TABLE 1

Formula # and Description of the Food

| Formula # | Formula Description |
|---|---|
| 1 | Control |
| 2 | Control plus calcium pyruvate |
| 3 | Control plus lipoic acid |
| 4 | Control plus lipoic acid and calcium pyruvate |

Table 2 illustrates four Pet Food Compositions used in the weight loss study. Formula 1 is a control that does not contain lipoic acid or pyruvate. Formula 2 is a Control plus calcium pyruvate. Formula 3 is a Control plus lipoic acid. Formula 4 is a Control plus lipoic acid and calcium pyruvate.

TABLE 2

Ingredient Composition of foods used

| Ingredient (Wt. % of food) | Formula 1 | Formula 2 | Formula 3 | Formula 4 |
|---|---|---|---|---|
| Corn | 29.4 | 27.8 | 29.1 | 27.5 |
| Poultry Meal | 19.4 | 19.5 | 19.4 | 19.5 |
| Corn Gluten Meal | 19.4 | 19.5 | 19.4 | 19.5 |
| Cellulose | 9.6 | 9.7 | 9.6 | 9.7 |
| Soy Mill Run | 9.6 | 9.5 | 9.6 | 9.5 |
| Beet Pulp | 4.3 | 4.3 | 4.3 | 4.3 |
| Pal Enhancer | 3.6 | 3.6 | 3.6 | 3.6 |
| Soybean Oil | 1.3 | 1.3 | 1.3 | 1.3 |
| Calcium pyruvate | — | 1 | — | 1 |

TABLE 2-continued

Ingredient Composition of foods used

| Ingredient (Wt. % of food) | Formula 1 | Formula 2 | Formula 3 | Formula 4 |
|---|---|---|---|---|
| Potassium Citrate | 0.9 | 1 | 0.9 | 1 |
| DL-Methionine | 0.6 | 0.6 | 0.6 | 0.6 |
| L-Lysine | 0.5 | 0.5 | 0.5 | 0.5 |
| Lipoic Acid | — | — | 0.3 | 0.3 |
| L-Carnitine | 0.2 | 0.3 | 0.2 | 0.3 |
| Vitamin E | 0.1 | 0.1 | 0.1 | 0.1 |
| Salt Iodized | 0.1 | 0.1 | 0.1 | 0.1 |
| Choline Chloride | 0.1 | 0.1 | 0.1 | 0.1 |
| Vitamin Premix | 0.1 | 0.1 | 0.1 | 0.1 |
| Preservative | 0.07 | 0.07 | 0.07 | 0.07 |
| Taurine | 0.07 | 0.07 | 0.07 | 0.07 |
| Mineral Mix | 0.07 | 0.07 | 0.07 | 0.07 |

Table 3 illustrates the nutrient values of each of the pet food compositions used in the study.

TABLE 3

Analyzed nutrient values of foods used in the study

| Nutrient (100% dry matter basis) | Formula 1 | Formula 2 | Formula 3 | Formula 4 |
|---|---|---|---|---|
| Crude Protein, % | 34.7 | 34.9 | 34.8 | 34.7 |
| Crude Fat, % | 8.7 | 9.1 | 8.6 | 8.8 |
| Ash, % | 5 | 5.3 | 5 | 5.3 |
| Calcium, % | 0.8 | 0.97 | 0.8 | 1 |
| Phosphorus, % | 0.67 | 0.67 | 0.65 | 0.69 |
| Potassium, % | 0.7 | 0.8 | 0.8 | 0.8 |
| Sodium, % | 0.26 | 0.23 | 0.23 | 0.24 |
| Chloride, % | 0.4 | 0.4 | 0.4 | 0.4 |
| Crude Fiber, % | 13.6 | 13.6 | 13.3 | 13.5 |
| Total Dietary Fiber, % | 25.8 | 26.6 | 26.5 | 27.5 |
| Insoluble Fiber, % | 24 | 24.9 | 23.4 | 24.5 |
| Soluble Fiber, % | 1.9 | 1.8 | 3.1 | 3 |
| Lysine, % | 1.8 | 1.8 | 1.8 | 1.9 |
| Pyruvic Acid, % | 0.0 | 0.22 | 0.0 | 0.23 |
| Lipoic Acid, ppm | — | — | 138 | 129 |

Table 4 illustrates predicted time to reach 20% body fat for dogs fed each of the pet food compositions.

TABLE 4

Predicted Time to Reach 20% Body Fat

| Months to Weight Loss Goal | Formula 1 | Formula 2 | Formula 3 | Formula 4 |
|---|---|---|---|---|
| | 5.07 +/− 2.72 | 5.48 +/− 2.12 | 7.58 +/− 2.77 | 4.79 +/− 1.78 |

| | Probability Associated with a Subject's Paired t-Test | | | |
|---|---|---|---|---|
| Formula 1 | — | 0.642 | 0.041 | 0.783 |
| Formula 2 | 0.642 | — | 0.059 | 0.410 |
| Formula 3 | 0.041 | 0.059 | — | 0.049 |
| Formula 4 | 0.783 | 0.410 | 0.049 | — |

The rate of fat loss for all dogs in the current study was linear ($R^2 > 0.87$ for each dog). As a result, the data was used to predict how long it would take for the dogs on average to achieve a weighs loss goal of 20% body fat. The food containing both lipoic acid and pyruvate has the shortest time on average to reach the weight loss goal of 20% body fat. In addition, this food also has the smallest standard deviation indicating less variation amongst the dogs.

Tables 5-14 illustrate the average physical and chemical characteristics of dogs fed each of the pet food compositions.

Table 5 illustrates that illustrative pet food composition including lipoic acid and calcium pyruvate resulted in reduced lean body mass in dogs fed the illustrative pet food composition over a four month period.

DNA Analysis

TABLE 5

Lean Body Mass (grams)

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 0 | 8 | 8505.95 ± 437 | 8 | 8764.70 ± 720 | 8 | 8873.39 ± 1032 | 8 | 8588.09 ± 1138 | NS* |
| Observed Month 1 | 8 | 8545.11 ± 450 | 8 | 8674.49 ± 648 | 8 | 8600.76 ± 1021 | 8 | 8379.35 ± 1104 | NS* |

TABLE 5-continued

Lean Body Mass (grams)

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 2 | 8 | 8482.50 ± 494 | 8 | 8674.95 ± 689 | 8 | 8626.30 ± 992 | 8 | 8422.71 ± 1105 | NS* |
| Observed Month 3 | 8 | 8534.54 ± 488 | 8 | 8727.70 ± 669 | 8 | 8541.00 ± 953 | 8 | 8518.20 ± 1087 | NS* |
| Observed Month 4 | 8 | 8672.64 ± 481 | 8 | 8848.52 ± 642 | 8 | 8636.60 ± 1001 | 8 | 8579.06 ± 1067 | NS* |
| Change from Month 0 to 1 | 8 | 39.16 ± 115 | 8 | −90.21 ± 113 | 8 | −272.63 ± 66.1 | 8 | −208.74 ± 122 | NS* |
| Change from Month 0 to 2 | 8 | −23.45 ± 143 | 8 | −89.75 ± 84.1 | 8 | −247.09 ± 119 | 8 | −165.37 ± 136 | NS* |
| Change from Month 0 to 3 | 8 | 28.59 ± 168 | 8 | −37.00 ± 69.4 | 8 | −332.39 ± 146 | 8 | −69.89 ± 152 | NS* |
| Change from Month 0 to 4 | 8 | 166.69 ± 151 | 8 | 83.82 ± 96.5 | 8 | −236.79 ± 112 | 8 | −9.03 ± 154 | NS* |
| Month 0 vs 1** | | NS* | | NS* | | <0.0100 | | NS* | |
| Month 0 vs 2** | | NS* | | NS* | | NS* | | NS* | |
| Month 0 vs 3** | | NS* | | NS* | | NS* | | NS* | |
| Month 0 vs 4** | | NS* | | NS* | | NS* | | NS* | |

*NS = Not significant (i.e. p-values > 0.1)
**Wilcoxin signed-rank test

Table 6 illustrates that illustrative pet food composition including lipoic acid and calcium pyruvate resulted in reduced percent body fat in dogs fed the illustrative pet food composition over a four month period.

TABLE 6

Percent Body Fat

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 0 | 8 | 40.43 ± 1.5 | 8 | 38.99 ± 1.01 | 8 | 40.59 ± 1.92 | 8 | 40.98 ± 1.11 | NS* |
| Observed Month 1 | 8 | 35.25 ± 2.3 | 8 | 35.36 ± 1.53 | 8 | 38.20 ± 2.18 | 8 | 36.71 ± 0.99 | NS* |
| Observed Month 2 | 8 | 31.05 ± 2.77 | 8 | 31.54 ± 1.85 | 8 | 34.84 ± 1.76 | 8 | 31.24 ± 1.18 | NS* |
| Observed Month 3 | 8 | 27.91 ± 2.14 | 8 | 28.45 ± 1.44 | 8 | 32.48 ± 2.06 | 8 | 26.25 ± 1.74 | NS* |
| Observed Month 4 | 8 | 25.11 ± 1.48 | 8 | 25.91 ± 1.5 | 8 | 30.58 ± 1.94 | 8 | 24.94 ± 1.33 | NS* |
| Month 0 to 1 | | NS* | | <0.0100 | | <0.46 | | −4.26 ± 0.72 | |
| Month 0 to 2 | | NS* | | <0.0100 | | <0.59 | | −9.74 ± 1.34 | |
| Change from Month 0 to 3 | 8 | −12.51 ± 1.31 | 8 | −10.54 ± 1.04 | 8 | −8.11 ± 0.79 | 8 | −14.73 ± 2.21 | 0.226 |
| Change from Month 0 to 4 | 8 | −15.31 ± 1.18 | 8 | −13.08 ± 1.45 | 8 | −10.01 ± 0.62 | 8 | −16.04 ± 1.9 | 0.0128 |
| Month 0 vs 1** | | <0.0100 | | <0.0100 | | <0.0100 | | <0.0100 | |
| Month 0 vs 2** | | <0.0100 | | <0.0100 | | <0.0100 | | <0.0100 | |
| Month 0 vs 3** | | <0.0100 | | <0.0100 | | <0.0100 | | <0.0100 | |

TABLE 6-continued

| | | Percent Body Fat | | | | | | | Treatment Effect (Kruskal-Wallis) |
|---|---|---|---|---|---|---|---|---|---|
| Parameter Measured | N | Formula 1 Mean ± SEM | N | Formula 2 Mean ± SEM | N | Formula 3 Mean ± SEM | N | Formula 4 Mean ± SEM | |
| Month 0 vs 4** | | <0.0100 | | <0.0100 | | <0.0100 | | <0.0100 | |

*NS = Not significant (ie. p-values > 0.1)
**Wilcoxin signed-rank test

Table 7 illustrates that illustrative pet food composition including lipoic acid and calcium pyruvate resulted in reduced total body fat is dogs fed the illustrative pet food composition over a four month period.

TABLE 7

| | | Total Body Fat (grams) | | | | | | | Treatment Effect (Kruskal-Wallis) |
|---|---|---|---|---|---|---|---|---|---|
| Parameter Measured | N | Formula 1 Mean ± SEM | N | Formula 2 Mean ± SEM | N | Formula 3 Mean ± SEM | N | Formula 4 Mean ± SEM | |
| Observed Month 0 | 8 | 6106.65 ± 341 | 8 | 5936.61 ± 540 | 8 | 6249.08 ± 679 | 8 | 6164.74 ± 696 | NS* |
| Observed Month 1 | 8 | 4954.41 ± 437 | 8 | 5065.91 ± 491 | 8 | 5454.59 ± 602 | 8 | 5070.16 ± 626 | NS* |
| Observed Month 2 | 8 | 4078.66 ± 442 | 8 | 4247.31 ± 424 | 8 | 4768.61 ± 529 | 8 | 4032.25 ± 572 | NS* |
| Observed Month 3 | 8 | 3515.89 ± 353 | 8 | 3671.10 ± 331 | 8 | 4269.15 ± 524 | 8 | 3259.35 ± 534 | NS* |
| Observed Month 4 | 8 | 3077.63 ± 264 | 8 | 3284.01 ± 324 | 8 | 3911.33 ± 454 | 8 | 3102.36 ± 525 | NS* |
| Change from Month 0 to 1 | 8 | −1152.2 ± 167 | 8 | −870.70 ± 189 | 8 | −794.49 ± 113 | 8 | −1094.6 ± 134 | NS* |
| Change from Month 0 to 2 | 8 | −2028.0 ± 213 | 8 | −1689.3 ± 288 | 8 | −1480.5 ± 176 | 8 | −2132.5 ± 248 | NS* |
| Change from Month 0 to 3 | 8 | −2590.8 ± 182 | 8 | −2265.5 ± 328 | 8 | −1979.9 ± 197 | 8 | −2905.4 ± 351 | NS* |
| Change from Month 0 to 4 | 8 | −3029.0 ± 196 | 8 | −2652.6 ± 385 | 8 | −2337.8 ± 254 | 8 | −3062.4 ± 291 | NS* |
| Month 0 vs 1** | | <0.0100 | | <0.0100 | | <0.0100 | | <0.0100 | |
| Month 0 vs 2** | | <0.0100 | | <0.0100 | | <0.0100 | | <0.0100 | |
| Month 0 vs 3** | | <0.0100 | | <0.0100 | | <0.0100 | | <0.0100 | |
| Month 0 vs 4** | | <0.0100 | | <0.0100 | | <0.0100 | | <0.0100 | |

*NS = Not significant (ie. p-values > 0.1)
**Wilcoxin signed-rank test

Table 8 illustrates that an illustrative pet food composition including lipoic acid and calcium pyruvate resulted in reduced total body weight in dogs fed the illustrative pet food composition over a four month period.

TABLE 8

Total Body Weight (grams)

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 0 | 8 | 15094.8 ± 666 | 8 | 15172.3 ± 1240 | 8 | 15580.1 ± 1665 | 8 | 15207.2 ± 1858 | NS* |
| Observed Month 1 | 8 | 13964.5 ± 678 | 8 | 14204.2 ± 1099 | 8 | 14503.7 ± 1555 | 8 | 13886.5 ± 1747 | NS* |
| Observed Month 2 | 8 | 13027.8 ± 681 | 8 | 13379.1 ± 1039 | 8 | 13839.2 ± 1481 | 8 | 12883.6 ± 1686 | NS* |
| Observed Month 3 | 8 | 12506.4 ± 687 | 8 | 12852.2 ± 946 | 8 | 13253.2 ± 1402 | 8 | 12199.9 ± 1612 | NS* |
| Observed Month 4 | 8 | 12202.9 ± 681 | 8 | 12582.5 ± 916 | 8 | 12986.4 ± 1401 | 8 | 12100.8 ± 1611 | NS* |
| Change from Month 0 to 1 | 8 | −1130.4 ± 125 | 8 | −968.06 ± 185 | 8 | −1076.4 ± 124 | 8 | −1320.7 ± 202 | NS* |
| Change from Month 0 to 2 | 8 | −2067.0 ± 135 | 8 | −1793.2 ± 287 | 8 | −1740.9 ± 198 | 8 | −2323.6 ± 293 | NS* |
| Change from Month 0 to 3 | 8 | −2588.4 ± 103 | 8 | −2320.1 ± 358 | 8 | −2326.8 ± 280 | 8 | −3007.3 ± 383 | NS* |
| Change from Month 0 to 4 | 8 | −2891.9 ± 137 | 8 | −2589.8 ± 412 | 8 | −2593.6 ± 288 | 8 | −3106.4 ± 364 | NS* |
| Month 0 vs 1** | | <0.0100 | | <0.0100 | | <0.0100 | | <0.0100 | |
| Month 0 vs 2** | | <0.0100 | | <0.0100 | | <0.0100 | | <0.0100 | |
| Month 0 vs 3** | | <0.0100 | | <0.0100 | | <0.0100 | | <0.0100 | |
| Month 0 vs 4** | | <0.0100 | | <0.0100 | | <0.0100 | | <0.0100 | |

*NS = Not significant (ie. p-values > 0.1)
**Wilcoxin signed-rank test

Chemistry Screens

Table 9 illustrates that an illustrative pet food composition including lipoic acid and calcium pyruvate resulted in reduced serum alanine aminotransferase levels in dogs fed the illustrative pet food composition over a four month period.

TABLE 9

Serum Alanine Aminotransferase

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 0 | 8 | 48.25 ± 11.4 | 8 | 43.75 ± 6.43 | 8 | 44.44 ± 8.52 | 8 | 54.63 ± 10.7 | NS* |
| Observed Month 1 | 8 | 40.88 ± 9.5 | 8 | 33.88 ± 3.94 | 8 | 35.50 ± 6.42 | 8 | 51.38 ± 17.5 | NS* |
| Observed Month 2 | 8 | 42.50 ± 13.2 | 8 | 34.50 ± 3.67 | 8 | 34.63 ± 6.11 | 8 | 44.88 ± 12.8 | NS* |
| Observed Month 3 | 8 | 43.63 ± 10.4 | 8 | 37.63 ± 5.28 | 8 | 34.00 ± 6.39 | 8 | 54.63 ± 13.8 | NS* |
| Observed Month 4 | 8 | 51.38 ± 12.7 | 8 | 40.38 ± 4.73 | 8 | 56.25 ± 16.9 | 8 | 41.50 ± 8.48 | NS* |
| Change from Month 0 to 1 | 8 | −7.38 ± 10.6 | 8 | −9.88 ± 7.57 | 8 | −11.00 ± 7.08 | 8 | −3.25 ± 8.33 | NS* |
| Change from Month 0 to 2 | 8 | −5.75 ± 14.2 | 8 | −9.13 ± 7.2 | 8 | −11.88 ± 7.34 | 8 | −9.75 ± 5.85 | NS* |
| Change from Month 0 to 3 | 8 | −4.63 ± 7.58 | 8 | −6.13 ± 8.4 | 8 | −12.50 ± 7.09 | 8 | 0.00 ± 13.6 | NS* |

TABLE 9-continued

Serum Alanine Aminotransferase

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Change from Month 0 to 4 | 8 | 3.13 ± 11 | 8 | −3.38 ± 8.16 | 8 | 9.75 ± 17.4 | 8 | −13.13 ± 4.83 | NS* |
| Month 0 vs 1** | | NS* | | NS* | | NS* | | NS* | |
| Month 0 vs 2** | | NS* | | NS* | | NS* | | NS* | |
| Month 0 vs 3** | | NS* | | NS* | | 0.0156 | | NS* | |
| Month 0 vs 4** | | NS* | | NS* | | NS* | | 0.0469 | |

*NS = Not significant (ie. p-values > 0.1)
**Wilcoxin signed-rank test

Table 10 illustrates that an illustrative pet food composition including lipoic acid and calcium pyruvate resulted its reduced serum alkaline phosphatase levels in dogs fed the illustrative pet food composition over a four month period.

TABLE 10

Serum Alkaline Phosphatase

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 0 | 8 | 243.38 ± 85.6 | 8 | 171.13 ± 72.3 | 8 | 124.56 ± 34.8 | 8 | 158.00 ± 64.1 | NS* |
| Observed Month 1 | 8 | 125.63 ± 47.4 | 8 | 83.38 ± 28.6 | 8 | 57.63 ± 7.38 | 8 | 72.63 ± 28.4 | NS* |
| Observed Month 2 | 8 | 111.50 ± 42.6 | 8 | 67.88 ± 17.9 | 8 | 52.25 ± 5.16 | 8 | 75.63 ± 28 | NS* |
| Observed Month 3 | 8 | 122.13 ± 41.3 | 8 | 68.63 ± 16.3 | 8 | 56.88 ± 3.98 | 8 | 75.00 ± 20.8 | NS* |
| Observed Month 4 | 8 | 111.00 ± 37.4 | 8 | 57.63 ± 11.7 | 8 | 51.25 ± 3.87 | 8 | 66.00 ± 17.2 | NS* |
| Change from Month 0 to 1 | 8 | −117.75 ± 39.3 | 8 | −87.75 ± 44.4 | 8 | −68.88 ± 33.6 | 8 | −85.38 ± 36.4 | NS* |
| Change from Month 0 to 2 | 8 | −128.38 ± 43.6 | 8 | −103.25 ± 55.3 | 8 | −74.25 ± 36.5 | 8 | −79.38 ± 41 | NS* |
| Change from Month 0 to 3 | 8 | −121.25 ± 44.8 | 8 | −102.50 ± 57.9 | 8 | −69.63 ± 38.9 | 8 | −83.00 ± 46.5 | NS* |
| Change from Month 0 to 4 | 8 | −132.38 ± 49.7 | 8 | −113.50 ± 63.7 | 8 | −75.25 ± 38.9 | 8 | −92.00 ± 50.8 | NS* |
| Month 0 vs 1** | | <0.0100 | | <0.0100 | | 0.0156 | | <0.0100 | |
| Month 0 vs 2** | | <0.0100 | | 0.0156 | | 0.0156 | | 0.0234 | |
| Month 0 vs 3** | | <0.0100 | | 0.0234 | | 0.0391 | | 0.0234 | |
| Month 0 vs 4** | | <0.0100 | | <0.0100 | | 0.0156 | | 0.0234 | |

*NS = Not significant (ie. p-values > 0.1)
**Wilcoxin signed-rank test

Table 11 illustrates that an illustrative pet food composition including lipoic acid and calcium pyruvate resulted in reduced serum cholesterol levels in dogs dm the illustrative pet food composition over a four month period.

TABLE 11

Serum Cholesterol

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 0 | 8 | 218.38 ± 14 | 8 | 191.25 ± 12.8 | 8 | 203.33 ± 12.7 | 8 | 238.75 ± 16.1 | NS* |
| Observed Month 1 | 8 | 158.25 ± 8.69 | 8 | 144.13 ± 12.6 | 8 | 146.00 ± 8.24 | 8 | 158.13 ± 12.2 | NS* |
| Observed Month 2 | 8 | 153.63 ± 6.76 | 8 | 146.00 ± 11.8 | 8 | 144.75 ± 8.3 | 8 | 159.88 ± 7.83 | NS* |
| Observed Month 3 | 8 | 154.75 ± 5.78 | 8 | 151.38 ± 11.4 | 8 | 145.25 ± 8.83 | 8 | 152.00 ± 8.04 | NS* |
| Observed Month 4 | 8 | 149.38 ± 5.37 | 8 | 144.63 ± 11.2 | 8 | 139.00 ± 9.22 | 8 | 149.75 ± 10 | NS* |
| Change from Month 0 to 1 | 8 | −60.13 ± 10.7 | 8 | −47.13 ± 8.29 | 8 | −58.50 ± 12 | 8 | −80.63 ± 10.7 | NS* |
| Change from Month 0 to 2 | 8 | −64.78 ± 12.3 | 8 | −45.25 ± 6.74 | 8 | −59.75 ± 9.67 | 8 | −78.88 ± 11.7 | NS* |
| Change from Month 0 to 3 | 8 | −63.63 ± 10.3 | 8 | −39.88 ± 7.02 | 8 | −59.25 ± 9.73 | 8 | −86.75 ± 10.4 | 0.0256 |
| Change from Month 0 to 4 | 8 | −69.00 ± 11 | 8 | −46.63 ± 6.38 | 8 | −65.50 ± 10.9 | 8 | −89.00 ± 9.64 | 0.0601 |
| Month 0 vs 1** | | <0.0100 | | <0.0100 | | <0.0100 | | <0.0100 | |
| Month 0 vs 2** | | <0.0100 | | <0.0100 | | <0.0100 | | <0.0100 | |
| Month 0 vs 3** | | <0.0100 | | <0.0100 | | <0.0100 | | <0.0100 | |
| Month 0 vs 4** | | <0.0100 | | <0.0100 | | <0.0100 | | <0.0100 | |

*NS = Not significant (ie. p-values > 0.1)
**Wilcoxin signed-rank test

Table 12 illustrates that illustrative pet food composition including lipoic acid and calcium pyruvate resulted in reduced serum creatinine levels in dogs fed the illustrative net food composition over a four month period.

TABLE 12

Serum Creatinine

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 0 | 8 | 0.61 ± 0.04 | 8 | 0.62 ± 0.04 | 8 | 0.70 ± 0.09 | 8 | 0.61 ± 0.04 | NS* |
| Observed Month 1 | 8 | 0.58 ± 0.03 | 8 | 0.50 ± 0.02 | 8 | 0.62 ± 0.04 | 8 | 0.54 ± 0.03 | NS* |
| Observed Month 2 | 8 | 0.59 ± 0.03 | 8 | 0.51 ± 0.02 | 8 | 0.60 ± 0.04 | 8 | 0.53 ± 0.03 | NS* |
| Observed Month 3 | 8 | 0.56 ± 0.04 | 8 | 0.46 ± 0.02 | 8 | 0.55 ± 0.03 | 8 | 0.48 ± 0.03 | 0.0774 |
| Observed Month 4 | 8 | 0.57 ± 0.03 | 8 | 0.45 ± 0.02 | 8 | 0.57 ± 0.03 | 8 | 0.49 ± 0.03 | 0.0135 |
| Change from Month 0 to 1 | 8 | −0.02 ± 0.02 | 8 | −0.12 ± 0.03 | 8 | −0.11 ± 0.08 | 8 | −0.08 ± 0.02 | 0.0530 |
| Change from Month 0 to 2 | 8 | −0.01 ± 0.02 | 8 | −0.11 ± 0.03 | 8 | −0.13 ± 0.09 | 8 | −0.08 ± 0.02 | 0.0388 |
| Change from Month 0 to 3 | 8 | −0.05 ± 0.01 | 8 | −0.16 ± 0.03 | 8 | −0.17 ± 0.09 | 8 | −0.13 ± 0.02 | 0.0221 |
| Change from Month 0 to 4 | 8 | −0.03 ± 0.02 | 8 | −0.17 ± 0.03 | 8 | −0.15 ± 0.09 | 8 | −0.13 ± 0.02 | 0.0244 |

TABLE 12-continued

Serum Creatinine

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Month 0 vs 1** | | NS* | | <0.0100 | | NS* | | 0.0156 | |
| Month 0 vs 2** | | NS* | | <0.0100 | | 0.0781 | | 0.0156 | |
| Month 0 vs 3** | | <0.0100 | | <0.0100 | | 0.01560 | | <0.0100 | |
| Month 0 vs 4** | | NS* | | <0.0100 | | 0.04690 | | <0.0100 | |

*NS = Not significant (ie. p-values > 0.1)
**Wilcoxin signed-rank test

Table 13 illustrates mat illustrative pet food composition including lipoic acid and calcium pyruvate resulted in reduced serum triglyceride levels in dogs fed the illustrative pet food composition over a four month period.

TABLE 13

Serum Triglycerides

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 0 | 8 | 189.38 ± 17 | 8 | 185.50 ± 21.3 | 8 | 218.78 ± 15.8 | 8 | 235.25 ± 17.2 | NS* |
| Observed Month 1 | 8 | 154.50 ± 12 | 8 | 170.63 ± 13.9 | 8 | 176.00 ± 10.1 | 8 | 152.75 ± 13.1 | NS* |
| Observed Month 2 | 8 | 125.63 ± 8.9 | 8 | 144.38 ± 8.44 | 8 | 148.88 ± 6.47 | 8 | 147.00 ± 19.7 | NS* |
| Observed Month 3 | 8 | 112.75 ± 9.1 | 8 | 127.50 ± 11.3 | 8 | 137.50 ± 6.98 | 8 | 123.38 ± 19.1 | NS* |
| Observed Month 4 | 8 | 126.63 ± 9.81 | 8 | 137.38 ± 11.2 | 8 | 122.25 ± 13.9 | 8 | 113.38 ± 14 | NS* |
| Change from Month 0 to 1 | 8 | −34.88 ± 21.6 | 8 | −14.88 ± 20.3 | 8 | −39.63 ± 16.3 | 8 | −82.50 ± 17.7 | NS* |
| Change from Month 0 to 2 | 8 | −64.88 ± 17.9 | 8 | −41.13 ± 18.6 | 8 | −66.75 ± 16.1 | 8 | −88.25 ± 18.2 | NS* |
| Change from Month 0 to 3 | 8 | −76.63 ± 10.5 | 8 | −58.00 ± 25 | 8 | −78.13 ± 13.2 | 8 | −111.88 ± 18.6 | NS* |
| Change from Month 0 to 4 | 8 | −62.75 ± 15.6 | 8 | −48.13 ± 19.9 | 8 | −93.38 ± 15.6 | 8 | −121.88 ± 16.7 | 0.0487 |
| Month 0 vs 1** | | NS* | | NS* | | 0.0625 | | <0.0100 | |
| Month 0 vs 2** | | 0.0156 | | 0.0547 | | 0.0156 | | 0.0156 | |
| Month 0 vs 3** | | <0.0100 | | 0.0391 | | 0.0156 | | <0.0100 | |
| Month 0 vs 4** | | 0.0156 | | 0.0781 | | <0.0100 | | <0.0100 | |

*NS = Not significant (ie. p-values > 0.1)
**Wilcoxin signed-rank test

Table 14 illustrates that illustrative pet food composition including lipoic acid and calcium pyruvate resulted in reduced serum area nitrogen levels in dogs fed the illustrative pet food composition over a four month period.

TABLE 14

Serum Urea Nitrogen

| Parameter Measured | N | Formula 1 Mean ± SEM | N | Formula 2 Mean ± SEM | N | Formula 3 Mean ± SEM | N | Formula 4 Mean ± SEM | Treatment Effect (Kruskal-Wallis) |
|---|---|---|---|---|---|---|---|---|---|
| Observed Month 0 | 8 | 11.71 ± 0.5 | 8 | 14.94 ± 3.33 | 8 | 13.92 ± 1.42 | 8 | 11.59 ± 1.14 | NS* |
| Observed Month 1 | 8 | 13.70 ± 0.78 | 8 | 14.70 ± 1.76 | 8 | 17.16 ± 1.73 | 8 | 14.45 ± 1.85 | NS* |
| Observed Month 2 | 8 | 13.30 ± 0.87 | 8 | 12.93 ± 0.89 | 8 | 16.66 ± 2.02 | 8 | 14.99 ± 1.66 | NS* |
| Observed Month 3 | 8 | 13.95 ± 0.81 | 8 | 12.69 ± 0.78 | 8 | 15.18 ± 1.16 | 8 | 14.09 ± 1.32 | NS* |
| Observed Month 4 | 8 | 14.54 ± 0.79 | 8 | 12.65 ± 0.9 | 8 | 15.36 ± 0.92 | 8 | 14.10 ± 1.32 | NS* |
| Change from Month 0 to 1 | 8 | 1.99 ± 0.8 | 8 | −0.24 ± 1.93 | 8 | 3.15 ± 0.78 | 8 | 2.86 ± 1 | NS* |
| Change from Month 0 to 2 | 8 | 1.59 ± 0.69 | 8 | −2.01 ± 2.64 | 8 | 2.65 ± 0.95 | 8 | 3.40 ± 1.32 | NS* |
| Change from Month 0 to 3 | 8 | 2.24 ± 0.79 | 8 | −2.25 ± 3.41 | 8 | 1.16 ± 1.49 | 8 | 2.50 ± 0.47 | NS* |
| Change from Month 0 to 4 | 8 | 2.83 ± 0.86 | 8 | −2.29 ± 3.54 | 8 | 1.35 ± 1.77 | 8 | 2.51 ± 0.45 | NS* |
| Month 0 vs 1** | | 0.0234 | | NS* | | <0.0100 | | 0.0156 | |
| Month 0 vs 2** | | 0.0547 | | NS* | | 0.0156 | | 0.0469 | |
| Month 0 vs 3** | | 0.0391 | | NS* | | NS* | | <0.0100 | |
| Month 0 vs 4** | | 0.0156 | | NS* | | NS* | | <0.0100 | |

*NS = Not significant (i.e., p-values > 0.1)

**Wilcoxin signed-rank test

The invention is nor to be limited in scope by the specific embodiments disclosed in the examples, which are intended as illustrations of a few aspects of the invention, and any embodiments, which are functionally equivalent, are within the scope or this invention. Indeed, various modifications of the invention in addition to those shown and described herein will become apparent to those skilled in the art and are intended to tail within the appended claims.

For any references that have been cued, the entire disclosures of which are incorporated herein by reference.

What is claimed is:

1. A composition comprising pyruvic acid or a salt thereof and lipoic acid or a salt thereof,
    wherein pyruvic acid or a salt thereof is present in the composition in an amount of 5 ppm to 20000 ppm on a dry matter basis, and
    wherein lipoic acid or a salt thereof is present in the composition in an amount of 10 ppm to 5000 ppm,
    wherein the composition is a food, a supplement, an animal treat, or a toy, and
    wherein the lipoic acid or a salt thereof forms a coating on the surface of the food, the supplement, the animal treat, or the toy or on the surface of a component of the food, the supplement, the animal treat, or the toy.

2. The composition of claim 1, wherein pyruvic acid or a salt thereof is present in the composition in an amount of 100 ppm to 2500 ppm.

3. The composition of claim 1, wherein lipoic acid or a salt thereof is present in the composition in an amount of 500 ppm to 1000 ppm.

4. The composition of claim 1, wherein the composition is a dog food.

5. The composition of claim 1, wherein the composition is a cat food.

6. The composition of claim 1, which is in the form of a moist food.

7. The composition of claim 1, which is in the form of a dry food.

8. The composition of claim 1, wherein lipoic acid or a salt thereof is present in the composition in an amount of 150 ppm to 5000 ppm.

9. The composition of claim 1, wherein pyruvic acid or a salt thereof is present in the composition in an amount of 5 ppm to 100 ppm on a dry matter basis, and wherein lipoic acid or a salt thereof is present in the composition in an amount of 100 ppm to 200 ppm.

10. The composition of claim 1, wherein pyruvic acid or a salt thereof is present in the composition in an amount of 2000 ppm to 3000 ppm on a dry matter basis, and wherein lipoic acid or a salt thereof is present in the composition in an amount of 100 ppm to 200 ppm.

11. The composition of claim 1, wherein the lipoic acid or salt thereof is incorporated on the surface by spraying thereon.

12. The composition of claim 1, wherein the lipoic acid or salt thereof is incorporated on the surface by precipitation thereon.

13. A method for managing weight in a companion animal, decreasing body fat in a companion animal, increasing lean body mass in a companion animal, or combinations thereof, which comprises administering to the companion animal a composition according claim 1.

* * * * *